US 7,727,204 B2

(12) United States Patent
Negrier et al.

(10) Patent No.: US 7,727,204 B2
(45) Date of Patent: Jun. 1, 2010

(54) DEVICE FOR DOSING A PRODUCT THAT IS INTENDED TO BE APPLIED TO THE SKIN

(75) Inventors: Sandrine Negrier, Paris (FR); Dominique Ducrest, Boulogne Billancourt (FR)

(73) Assignee: Galderma S.A., Cham (CH)

( * ) Notice: Subject to any disclaimer, the term of this patent is extended or adjusted under 35 U.S.C. 154(b) by 163 days.

(21) Appl. No.: 10/582,214

(22) PCT Filed: Dec. 2, 2004

(86) PCT No.: PCT/FR2004/003100

§ 371 (c)(1),
(2), (4) Date: Mar. 23, 2007

(87) PCT Pub. No.: WO2005/055992

PCT Pub. Date: Jun. 23, 2005

(65) Prior Publication Data
US 2007/0191792 A1    Aug. 16, 2007

(30) Foreign Application Priority Data
Dec. 8, 2003    (FR) .................................. 03 14335

(51) Int. Cl.
*A61M 35/00*    (2006.01)
(52) U.S. Cl. .................. 604/289; 604/310; 604/191
(58) Field of Classification Search .............. 604/289, 604/191, 308–310, 306
See application file for complete search history.

(56) References Cited
U.S. PATENT DOCUMENTS

| 432,798 | A | * | 7/1890 | Hirst | 604/308 |
| 532,359 | A | * | 1/1895 | Bradley | 604/289 |
| 1,081,148 | A | * | 12/1913 | Quayle | 604/308 |
| 2,157,543 | A | * | 5/1939 | Kingman | 401/183 |
| 2,233,811 | A | * | 3/1941 | Doty | 604/289 |
| 2,795,043 | A | * | 6/1957 | Fleischer | 30/123.3 |
| 2,807,262 | A | * | 9/1957 | Lew | 602/47 |
| 2,990,563 | A | * | 7/1961 | Davidson | 401/126 |
| 3,033,420 | A | * | 5/1962 | Thomas et al. | 222/1 |
| 3,128,920 | A | * | 4/1964 | Volckening | 222/215 |
| 3,502,089 | A | * | 3/1970 | Paradis | 132/294 |
| 3,508,878 | A | * | 4/1970 | Gunders | 422/73 |

(Continued)

FOREIGN PATENT DOCUMENTS

EP    1 354 591    10/2003

(Continued)

OTHER PUBLICATIONS

Commission De La Transparence: "Silkis Laboratoires Galderma", pp. 1-7, Feb. 19, 2003.

*Primary Examiner*—Leslie R. Deak
*Assistant Examiner*—Paula L Craig
(74) *Attorney, Agent, or Firm*—Oblon, Spivak, McClelland, Maier & Neustadt, L.L.P.

(57) ABSTRACT

The present invention concerns a device for metering products intended to be applied to the skin, in particular pharmaceutical or cosmetic compositions. The invention relates more particularly to a device taking the form of an applicator stick, the graduations of which allow users to determine precisely the quantity of medication to be applied to the skin as a function of the surface area to be treated.

14 Claims, 2 Drawing Sheets

U.S. PATENT DOCUMENTS

| | | | |
|---|---|---|---|
| 3,572,337 A * | 3/1971 | Schunk | 604/77 |
| 3,749,084 A * | 7/1973 | Cucchiara | 600/575 |
| 3,894,531 A * | 7/1975 | Saunders, Jr. | 600/556 |
| 4,140,409 A * | 2/1979 | DeVries | 401/132 |
| 4,282,986 A * | 8/1981 | af Ekenstam et al. | 222/1 |
| 4,421,127 A * | 12/1983 | Geer | 132/294 |
| 4,486,194 A | 12/1984 | Ferrara | |
| 4,522,622 A | 6/1985 | Peery et al. | |
| 4,583,982 A * | 4/1986 | Vlock | 604/310 |
| 4,619,654 A * | 10/1986 | Abplanalp | 604/890.1 |
| 4,666,441 A * | 5/1987 | Andriola et al. | 424/448 |
| 4,751,934 A * | 6/1988 | Moir et al. | 132/319 |
| 4,781,705 A * | 11/1988 | Shepherd et al. | 604/289 |
| 4,786,282 A * | 11/1988 | Wagle et al. | 604/307 |
| 4,787,374 A * | 11/1988 | DeYarman | 601/154 |
| 4,813,404 A * | 3/1989 | Vallis | 601/125 |
| 4,887,611 A * | 12/1989 | Rudiger et al. | 600/556 |
| 4,995,408 A * | 2/1991 | Wallschlaeger | 132/320 |
| 5,086,791 A * | 2/1992 | Ferrari | 132/200 |
| 5,092,354 A * | 3/1992 | Pacelli, Jr. | 132/294 |
| 5,106,221 A * | 4/1992 | Diot et al. | 401/132 |
| 5,122,127 A * | 6/1992 | Stanley | 604/890.1 |
| 5,147,337 A * | 9/1992 | Plone | 604/306 |
| 5,224,787 A * | 7/1993 | Vasas | 401/119 |
| 5,242,433 A * | 9/1993 | Smith et al. | 604/289 |
| 5,259,835 A * | 11/1993 | Clark et al. | 602/48 |
| 5,308,343 A * | 5/1994 | Gafner | 604/289 |
| 5,334,189 A * | 8/1994 | Wade | 604/890.1 |
| 5,368,581 A * | 11/1994 | Smith et al. | 604/290 |
| 5,377,879 A * | 1/1995 | Isaacs | 222/205 |
| 5,394,907 A * | 3/1995 | Hjertman et al. | 141/1 |
| 5,470,323 A * | 11/1995 | Smith et al. | 604/289 |
| 5,520,202 A * | 5/1996 | Arbree | 132/294 |
| 5,632,728 A * | 5/1997 | Hein | 604/46 |
| 5,645,852 A * | 7/1997 | Newmark | 424/439 |
| 5,676,643 A * | 10/1997 | Cann et al. | 604/1 |
| 5,730,721 A * | 3/1998 | Hyatt et al. | 604/500 |
| 6,054,120 A * | 4/2000 | Burgoyne et al. | 424/59 |
| 6,056,729 A * | 5/2000 | Yu et al. | 604/289 |
| D427,371 S * | 6/2000 | Girardot et al. | D28/7 |
| 6,070,598 A * | 6/2000 | Gueret | 132/320 |
| 6,221,384 B1 * | 4/2001 | Pagedas | 424/449 |
| 6,284,234 B1 * | 9/2001 | Niemiec et al. | 424/78.07 |
| 6,315,482 B1 * | 11/2001 | Girardot et al. | 401/266 |
| 6,386,210 B1 * | 5/2002 | Slater | 132/294 |
| 7,122,712 B2 * | 10/2006 | Lutri et al. | 602/43 |
| 2003/0034044 A1 * | 2/2003 | Gubernick | 132/294 |
| 2004/0071494 A1 * | 4/2004 | Staniforth et al. | 401/262 |

FOREIGN PATENT DOCUMENTS

| | | | |
|---|---|---|---|
| FR | 2 593 401 | | 7/1987 |
| GB | 2279254 A | * | 1/1995 |
| WO | 03/092784 | | 11/2003 |

* cited by examiner

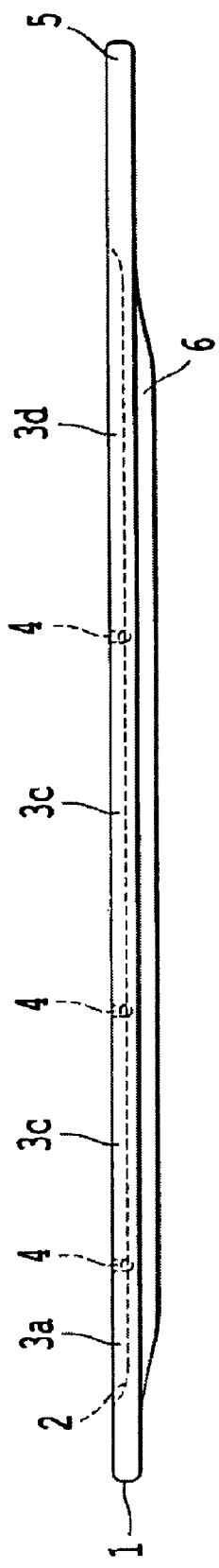
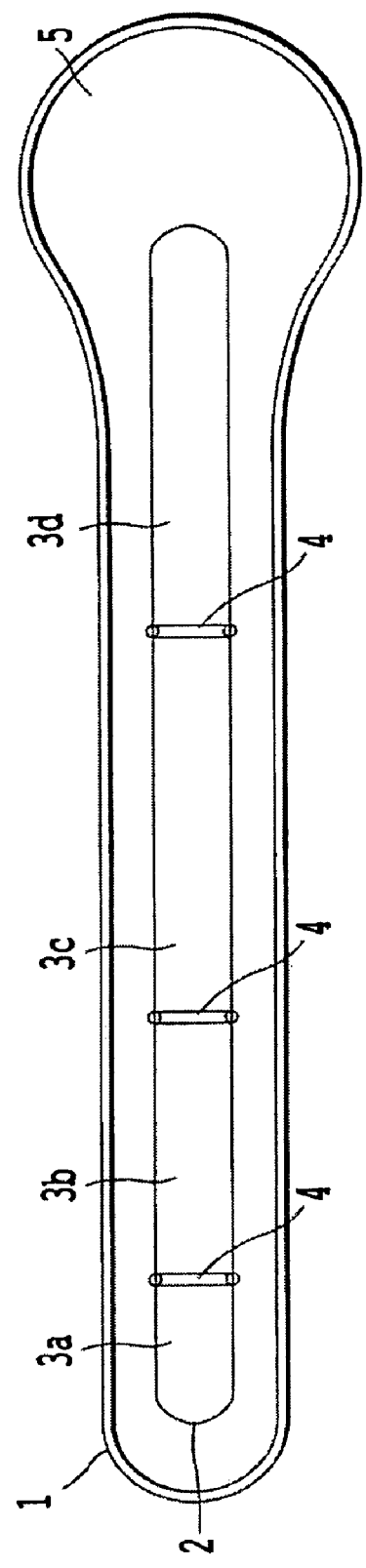

DEVICE FOR DOSING A PRODUCT THAT IS INTENDED TO BE APPLIED TO THE SKIN

The present invention concerns the metering of a product for topical application such as a medication. The invention is intended to provide a new device for metering products intended to be applied to the skin, in particular pharmaceutical or cosmetic products. The invention relates more particularly to a device taking the form of an applicator stick, the graduations of which allow users to determine the precise quantity of medication to be applied to the skin as a function of the surface area to be treated.

With regard to medication intended to be applied to the skin, it is known that the efficacy of topical medication depends inter alia on their dosage. Whether formulated as a cream, ointment, foam, liquid, or as adhesives such as patches, the medication intended for topical application is not packed in a device allowing optimum metering. Thus when the medication intended for topical application is packed in the form of a tube or simple bottle, the precise dose to be applied of said drug cannot be calibrated by the user.

There are however numerous metering distributors. Some have a siphon-like device which require pumping-like manipulation by the user; they often comprise a high number of parts which makes production difficult. Other metering distributors are fitted with a piston-type device but as the quantity of product supplied is a function of the pressure exerted by the user, these are not reliable.

Furthermore these metering distributors are fitted with a system allowing issue of only a single dose of the product.

To remedy the above drawbacks, the applicant has now developed an optimum device for metering a medication intended to be applied to the skin, where the quantity of medication applied is precise and can be modulated as a function of the surface of the skin to be treated; this allows better efficacy of the treatment.

This aim is achieved thanks to a device for metering a product intended to be applied to the skin, in particular a pharmaceutical or cosmetic composition, comprising an applicator stick with a longitudinal groove along which is defined a series of compartments, said groove being able to hold a quantity of medication corresponding to a defined surface area of the skin to be treated, the quantity being defined by one or more compartments.

Advantageously the applicator is fitted with graduations which, from one end of the groove corresponding to the start of the first compartment and for the following compartments, define the quantity of medication in the compartments of the groove.

Following a particular method of implementation, the device of the present invention comprises at least two, preferably at least three and most preferably four compartments.

Said compartments may have the same or different dimension and in the latter case compartments of increasing dimension are preferred. The term dimension here preferably means the length of the compartment but a variant of the invention consists of varying the depth or width of the groove continuously or from one compartment to the other.

Preferably the graduation of the applicator stick is selected from a graduated scale, protuberances, notches, a set of colours or a combination thereof. The graduation of the applicator stick may be arranged inside and/or outside the groove.

According to a particular method of implementation, the device preferably comprises at least one end of the applicator stick, a surface designed for manipulation. This may for example be a flared portion at one end of the applicator stick.

According to preferred embodiments of the invention:

the first compartment is able to contain a quantity of medication corresponding approximately to an area of 0.8 to 1.2% of the total surface of the body, preferably around 1% of the total surface of the body;

the first and second compartments are able to contain a quantity of medication corresponding approximately to an area of 2.4 to 3.6% of the total surface of the body, preferably around 3% of the total surface of the body;

the first, second and third compartments are able to contain a quantity of medication corresponding approximately to an area of 4.8 to 7.1% of the total surface of the body, preferably around 6% of the total surface of the body;

the first, second, third and fourth compartments are able to contain a quantity of medication corresponding approximately to an area of 7.2 to 10.8% of the total surface of the body, preferably 9% of the total surface of the body.

The device according to the invention is remarkable in that it can be reused by the patient, it is adapted to any form of presentation of the drugs for topical application, for example liquid, semi-liquid, gel, ointment, cream or powder.

The device according to the invention can be made of any impermeable material meeting hygiene requirements, such as glass, metal, flexible or rigid plastics.

A specific application of the device according to the invention relates to metering of a drug intended to treat psoriasis, said drug preferably being Silkis (calcitriol ointment).

For this application:

the first compartment is able to contain a quantity of Silkis (calcitriol ointment) of around 0.35 to 0.54 grams (g), preferably 0.45 grams;

the first and second compartments are able to contain a quantity of Silkis (calcitriol ointment) of around 1.08 to 1.62 grams, preferably 1.30 grams;

the first, second and third compartments are able to contain a quantity of Silkis (calcitriol ointment) of around 2.16 to 3.20 grams, preferably 2.60 grams;

the first, second, third and fourth compartments are able to contain a quantity of Silkis (calcitriol ointment) of around 3.24 to 4.86 grams, preferably 3.90 grams;

Other advantages and features of the invention will appear from the example below concerning a device for metering Silkis (calcitriol ointment) for the treatment of psoriasis, given as an illustrative example and not to be interpreted as limiting the scope of the invention, and in which reference will be made to the attached drawings in which:

FIG. 2 shows a top view of the metering device.

FIG. 3 shows a profile view of the metering device.

FIGS. 1, 2 and 3 represent a metering device according to the invention comprising an applicator stick (1) of oblong shape provided with graduations formed by protuberances (4). The applicator stick comprises a longitudinal groove (2) fitted with a series of compartments (3) and having at one end a flared circular part (5), which facilitates handling of said applicator stick.

Figure 1:
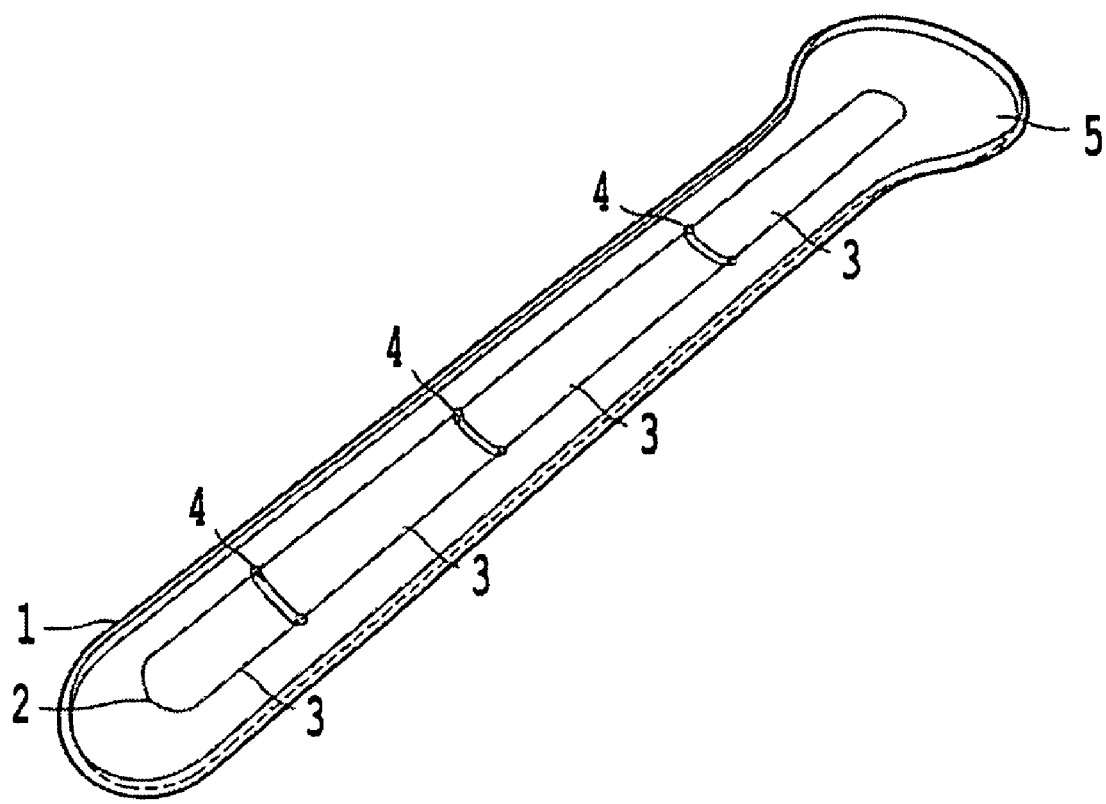
FIG. 1 shows an oblique top view of the metering device.

In the present example the applicator stick (1) is of oblong shape measuring 158 mm long, 32 mm wide at the level of the end with the circular portion (5) and 17 mm wide at the other end. The groove (2), of width 7 mm and depth 2 mm, extends along a longitudinal axis over 126 mm. This groove is divided into four compartments (3a, 3b, 3c and 3d) by protuberances (4). The first compartment (3a) defines a volume of 7 mm width, 2 mm depth and 14 mm length. The second compartment (3b) defines a volume of 7 mm width, 2 mm depth and 28 mm length. The third (3c) and fourth (3d) compartment each define a volume of 7 mm width, 2 mm depth and 42 mm length.

Figure 4:
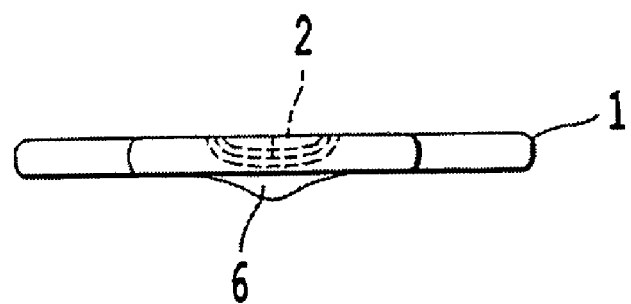
FIG. 4 shows a vertical section through the metering device.

FIGS. 3 and 4 show a metering device according to the invention with a longitudinal bulge (6) on the lower face of the applicator stick (1), which constitutes the base of the groove (2) or a means allowing inclination of the device when flat.

EXAMPLE 1

1) Definition of Body Surfaces to be Treated

To define the body surfaces to be treated in the treatment of psoriasis, the applicant uses a proposition derived from Wallace's 9% rule. The applicant has thus determined the following body surface area percentages (expressed in relation to the total surface area of the body):
  inguinal fold: between abdomen and thigh=1%
  gluteal fold=1% (3% of back)
  lumbar region=3%
  face=9%:1% per ear, 1% per eyebrow, 1% chin, 1% per nasal fold, 2% forehead 2) Determination of Silkis (Calcitriol Ointment) Dose Given that the maximum dose of Silkis (calcitriol ointment) that can be used per day is 30 grams in two applications and the maximum treatable surface area of the body is 35% of the total body surface, the applicant has established the optimum dose of Silkis (calcitriol ointment) as 30/2/35% or 0.43 grams per percentage body surface to be treated per application.

Table 1 shows the correlation between the percentage of body surface to be treated and the Silkis (calcitriol ointment) dose.

TABLE 1

|  | % body surface | | | |
| --- | --- | --- | --- | --- |
|  | 1% | 3% | 6% | 9% |
| Silkis (calcitriol ointment) dose | 1 | 3 | 6 | 9 |
| Quantity of Silkis (calcitriol ointment) to be applied (in g) | 0.45 | 1.30 | 2.60 | 3.90 |

The invention claimed is:

1. A metering device for a product intended to be applied to skin, in particular a pharmaceutical or cosmetic composition, comprising:
  an applicator stick that includes
    a longitudinal groove divided into a series of compartments and
    graduations provided perpendicular to the groove, that extend from a top surface of the applicator stick in a depth direction of the groove,
  wherein said groove accommodates a quantity of composition corresponding to a defined surface area of skin to be treated,
  wherein said quantity of composition is defined by the series of compartments, and
  wherein the groove defines an uncovered depression in the top surface of the applicator stick such that an entirety of the groove is exposed opposite the depression; wherein:
    one end of the groove corresponds to a start of a first compartment;
    the graduations divide the groove into the series of compartments;
    the graduations define the quantity of composition in each of the series of compartments of the groove;
    a volume of each of the compartments is defined by a length of the compartment in the axial direction;
    the applicator stick includes a flared circular portion and a narrow portion;
    the narrow portion extends from a first end of the applicator stick to the flared circular portion in an axial direction of the groove;
    the circular portion extends beyond the groove in an axial direction of the groove to a second end of the applicator stick;
    the circular portion includes a greater width than the narrow portion in a transverse direction of the applicator stick;
    the circular portion is dimensioned and configured so as to facilitate handling the applicator stick; and
    the composition is calcitriol ointment.

2. The metering device according claim 1, wherein the groove includes a first compartment, a second compartment, a third compartment, and a fourth compartment.

3. The metering device according to claim 1, wherein the first compartment is able to contain a quantity of composition corresponding to an area of 0.8 to 1.2% of a total surface of a body.

4. The metering device according to claim 2, wherein the first compartment and the second compartment are able to contain a combined quantity of composition corresponding to an area of 2.4 to 3.6% of a total surface of a body.

5. The metering device according to claim 2, wherein the first compartment, the second compartment, and the third compartment are able to contain a combined quantity of composition corresponding to an area of 4.8 to 7.1% of a total surface of a body.

6. The metering device according to claim 2, wherein the first compartment, the second compartment, the third compartment, and the fourth compartment are able to contain a combined quantity of composition corresponding to an area of 7.2 to 10.8% of a total surface of a body.

7. Device according to claim 2, wherein the first compartment is able to contain a quantity of 0.35 g to 0.54 g of calcitriol ointment.

8. The metering device according to claim 2, wherein the first compartment and the second compartment are able to contain a combined quantity of 1.08 g to 1.62 g of calcitriol ointment.

9. The metering device according to claim 2, wherein the first compartment, the second compartment, and the third compartment are able to contain a combined quantity of 2.16 g to 3.20 g of calcitriol ointment.

10. The metering device according to claim 2, wherein the first compartment, the second compartment, the third compartment, and the fourth compartment are able to contain a combined quantity of 3.24 g to 4.86 g of calcitriol ointment.

11. The metering device for metering a drug intending to be applied to the skin according to claim 1, wherein the groove has a uniform cross sectional area in an axial direction of the groove.

12. The metering device for metering a drug intending to be applied to the skin according to claim 1, wherein the groove has a constant depth and a constant width perpendicular to the axial direction of the groove.

13. The metering device for metering a drug intending to be applied to the skin according to claim 1, wherein each compartment in the series of compartments has a successively larger volume.

14. The metering device for metering a drug intending to be applied to the skin according to claim 1,
wherein the applicator stick includes a lower surface on an opposite side of the applicator stick with respect to the top surface, and
wherein the groove defines a bulge on the lower surface of the applicator stick such that the metering device is inclined when placed on a flat surface.

* * * * *